United States Patent [19]

Hoelderich et al.

[11] Patent Number: 4,474,741

[45] Date of Patent: Oct. 2, 1984

[54] PREPARATION OF A CRYSTALLINE ALUMINOSILICATE (ZEOLITE)

[75] Inventors: Wolfgang Hoelderich, Frankenthal; Laszlo Marosi, Ludwigshafen; Wolf D. Mross, Frankenthal; Matthias Schwarzmann, Limburgerhof, all of Fed. Rep. of Germany

[73] Assignee: BASF Aktiengesellschaft, Fed. Rep. of Germany

[21] Appl. No.: 316,070

[22] Filed: Oct. 28, 1981

[30] Foreign Application Priority Data

Nov. 6, 1980 [DE] Fed. Rep. of Germany ....... 3041847

[51] Int. Cl.$^3$ ............................................. C01B 33/28
[52] U.S. Cl. .................................. 423/329; 423/328; 502/64
[58] Field of Search ............................... 423/328–330; 252/455 Z; 260/448 C

[56] References Cited

U.S. PATENT DOCUMENTS 3,313,594  4/1967  Wilson ................................ 423/329
3,702,886  11/1972  Argauer et al. ...................... 423/328
4,126,574  11/1978  Reinwald et al. ............... 423/329 X

OTHER PUBLICATIONS

Derouane et al., "Molecular Shape-Selectivity of ZSM-5, Modified ZSM-5 and ZSM-11 Type Zeolites", *Faraday Discussion*, 72—72/19, pp. 1–13, 1981.

Jacobs et al., "Shape-Selectivity Changes in High-Silica Zeolites", pp. 353–369, 1981.

Jacobs et al., "Properties of the End Members in the Pentasil-Family of Zeolites: Characterization as Adsorbents", *Zeolites*, vol. 1, pp. 161–168, Oct. 1981.

Kokotailo et al., "Pentasil Family of High-Silica Crystalline Materials", *The Properties and Applications of Zeolites*, Chemical Society Special Publication, No. 33, pp. 132–139, 1980.

Wolf et al., "Zeitschrift fur chemie", 13 Jg. 1973, pp. 109–110.

*Primary Examiner*—Edward J. Meros
*Assistant Examiner*—Jackson Leeds
*Attorney, Agent, or Firm*—Keil & Witherspoon

[57] ABSTRACT

A process for the preparation of a crystalline aluminosilicate of the pentasil type by hydrothermal crystallization of $SiO_2$ and $Al(OH)_3$ in the presence of an alkali metal salt at from 80° to 250° C., wherein the crystallization is carried out in ether or aqueous ether. Particularly suitable solvents include the ethers from the group of the poly-(ethylene glycol) dimethyl ethers and mixtures of these ethers with water. The use of these crystalline aluminosilicates as catalysts for alkylating aromatics, and for preparing olefins and/or aromatics from methanol and/or dimethyl ether is also described.

8 Claims, No Drawings

PREPARATION OF A CRYSTALLINE ALUMINOSILICATE (ZEOLITE)

The present invention relates to a process for the preparation of a crystalline aluminosilicate of the pentasil type.

Crystalline aluminosilicates, such as zeolites, of natural or synthetic origin, have proved to be effective catalysts for various types of hydrocarbon conversions, for example hydrocarbon cracking. However, zeolites are also used industrially as ion exchangers and as molecular sieves.

Crystalline aluminosilicates, such as zeolites, have a highly ordered structure comprising a rigid three-dimensional lattice of $SiO_4$ and $AlO_4$ tetrahedra, which are joined by shared oxygen atoms. The ratio of Si and Al atoms to oxygen is 1:2. The electro-valency of the aluminum-containing tetrahedra is counterbalanced by inclusion of cations, for example alkali metal ions or hydrogen ions, in the crystal. Cation exchange is possible. Before dehydration by drying and/or calcining, the spaces between the tetrahedra are occupied by water molecules.

In recent years crystalline aluminosilicates having a high $SiO_2/Al_2O_3$ ratio of $\geq 11$ have generated increasing interest. Such zeolites are distinguished by high heat stability and exceptionally high acidity. Zeolites having a pentasil structure are synthesized in a conventional manner from a silicon component and an aluminum component in the presence of bulky quaternary organic ammonium compounds and alkali metal compounds as mineralizing agents. An example of such a process is to be found in U.S. Pat. No. 3,702,886. The large ammonium ions supposedly act as a template for the desired zeolite structure and permit the synthesis of crystalline aluminosilicates having $SiO_2/Al_2O_3$ ratios of greater than 100, for example up to 3,000. Such zeolites can be used, for example, to carry out the conversion of methanol, by carbon linking, to olefins (U.S. Pat. No. 3,911,041), or to catalyze the alkylation of benzene with ethylene, to give ethylbenzene (U.S. Pat. No. 3,751,504).

The use of quaternary amines as solvents presents problems in industrial operation. The odor nuisance and irritant action of the amines require extensive safety measures. A proportion of the amine undergoes decomposition during the synthesis and is thus lost as regards use in subsequent syntheses.

We have found that crystalline aluminosilicates of the pentasil type (zeolites) can be prepared more simply and without the above disadvantages by hydrothermal crystallization of $SiO_2$ and $Al(OH)_3$ in the presence of alkali metal salts at from 80° to 250° C., if the crystallization is carried out in an ether or aqueous ether.

In a preferred embodiment of the synthesis of these amine-free crystalline aluminosilicates (zeolites), a reaction mixture of $SiO_2$, for example commercial pyrogenic silica, freshly precipitated $Al(OH)_3$ and NaOH is reacted, in a 50:50 by weight ether/water mixture, for from 3 to 5 days, at from 150° to 170° C., under autogenous pressure in a stirred autoclave. The reaction product first obtained may, before calcination, still contain ether in place of the $H_2O$ molecules normally present in the intra-crystalline pores. The calcination removes all residues of organic compounds, so that only the free alkali metal ions remain in the crystalline aluminosilicate.

The molar ratio of $SiO_2$ to $Al_2O_3$ in the reaction mixture is from 20 to 200, preferably from 40 to 75.

The proportion of alkali metal hydroxide is from 1 to 3 moles per molar equivalent of $Al_2O_3$, preferably about 1.5 moles. Nucleating crystals can also be added to guide and accelerate the reaction.

The solvents used comprise ethers in general, including both linear and cyclic ethers containing a (—CH$_2$—CH$_2$—O) group, eg. monoethylene, diethylene, triethylene and tetraethylene glycol dimethyl ethers (glymes), diethyl ether, tetrahydrofuran, dioxane, mixtures of triethylene to decaethylene glycol methyl isopropyl ethers of mean degree of oxyethylation=5.5, ie. of the formula $CH_3O$—$(CH_2$—$CH_2$—$O)_{5.5}$—$C_3H_7$, diethylene glycol methyl isopropyl ether, a mixture of polyethylene glycol methyl isopropyl ethers of mean degree of oxyethylation 21, a mixture of triethylene to decaethylene glycol dimethyl ethers of mean degree of oxyethylation 5.5, ie. of the formula $CH_3O$(—$CH_2$—$CH_2$—$O)_{5.5}$—$CH_3$, a mixture of oxyethylated oxo-alcohols of mean molecular weight 200, 600 or 6,000, linear ethers containing a

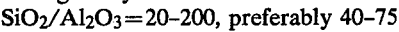

group as well as linear ethers having a (—CH$_2$—O) group, eg. dimethoxymethane (known commercially as Methylal). If commercial ether mixtures, eg. Sepasolv, Selexol or one of the Pluriols, are used, the process of preparation proves more difficult than if ethers having a defined chain length are employed. If one of the glymes (monoglyme to tetra-glyme) or tetrahydrofuran is used as the solvent, pure crystalline aluminosilicates with well-formed crystals are obtained, the habit of the crystals depending on the choice of ether. The formation of well-formed crystals of size 2 μm–15 μm is an advantage of this method of preparation in ethers.

The molar composition of the reaction mixture is advantageously selected so that:
$SiO_2/Al_2O_3 = 20$–200, preferably 40–75
$M_2O/Al_2O_3 \geq 1$, preferably 1.5–2 and
$ROR/Al_2O_3 = 18$–390,
where M is an alkali metal, especially Na, and ROR is an ether. The concentration of the ethers in water can be from 10 to 100% by weight, preferably about 50% by weight.

The process according to the invention is in general carried out at from 100° to 250° C., preferably from 150° to 190° C. The reaction time depends, inter alia, on the temperature and on whether nucleating crystals are added. For example, at from 150° to 190° C. it can be from 1 to 5 days. The reaction is advantageously carried out under autogenous pressure, in a stirred autoclave made from Hastelloy.

After the reaction, the product is advantageously filtered off, thoroughly washed with water and dried for 16 hours at 110° C. The product is then calcined for 20 hours at 550° C. in order to burn out any occluded ether and to dehydrate the zeolite. The conversion of the Na from to the catalytically active H form can be effected by conventional exchange methods, for example with ammonium salts.

The general formula of the crystalline aluminosilicate (zeolite) is:

$$0.01–1.3 Na_2O : Al_2O_3 : \geq 15 SiO_2 : 0–45 H_2O.$$

The zeolite prepared according to the invention in ether exhibit an X-ray diffraction diagram which shows them to be members of the pentasil family. The ether mother liquor can be used for further syntheses. The zeolites, which after exchange are obtained in the H-form, can be made into extrudates with matrix materials, for example Pural SB, up to a ratio of 90:10, and be employed as catalysts for hydrocarbon conversions, for example for the gas phase alkylation of benzene with ethylene to give ethylbenzene, at from 300° to 450° C., with a WHSV of 1-10 h$^{-1}$ (based on $C_6H_6$) and a $C_6H_6:C_2H_4$ ratio of 1-7, or for the conversion of alcohols and ethers, especially methanol and/or dimethyl ether, to olefins at from 350°-450° C., with a WHSV of 0.5-10 h$^{-1}$ (based on $CH_3OH$).

The analytical data in the Examples are based on solids. Before chemical analysis, the substances were calcined at 550° C. for 20 hours. The difference from 100% is accounted for by adsorbed water.

EXAMPLES 1-10

80 g of Aerosil are stirred into 1,000 g of a 50:50 ether/$H_2O$ mixture at 60° C. [suspension 1]. Al(OH)$_3$ is precipitated from 25 g of Al(NO$_3$)$_3$.9H$_2$O by means of NH$_3$. This freshly precipitated Al(OH)$_3$ is filtered off, thoroughly washed with water and suspended in 200 g of a 50:50 ether/$H_2O$ mixture. This suspension is introduced into suspension 1. 3.4-5.3 g of NaOH dissolved in 20 g of $H_2O$ are then added. This in most cases causes thickening of the reaction mixture. The mixture, stirred to render it homogeneous, is reacted for 5 days at 150°-170° C. in a stirred autoclave, made of Hastelloy, under autogenous pressure. When the reaction mixture has cooled, the crystalline product is filtered off, washed with 10 liters of $H_2O$, dried for 16 hours at 110° C. and calcined for 20 hours at 500° C.

Examples 1-10 are listed in Table 1.

EXAMPLES 11-13

Examples 11-13 relate to the preparation of zeolites in diglyme diethylene glycol dimethyl ether), using varying ratios of $SiO_2/Al_2O_3$.

TABLE 1

| Example | Ether | $SiO_2/Al_2O_3$ ratio employed | Pentasil type % | $SiO_2$ found % | $Al_2O_3$ found % | $SiO_2/Al_2O_3$ found | Na$^+$ found % |
|---|---|---|---|---|---|---|---|
| 1 | Ethylene glycol dimethyl ether | 40 | 100 | 90.2 | 4.0 | 38.2 | 2.0 |
| 2 | Diethylene glycol dimethyl ether | 40 | 100 | 92.2 | 3.6 | 43.9 | 2.0 |
| 3 | Triethylene glycol dimethyl ether | 40 | 100 | 93.1 | 3.47 | 45.6 | 1.84 |
| 4 | Tetraethylene glycol dimethyl ether | 40 | 100 | 92.9 | 3.24 | 48.7 | 1.55 |
| 5 | Tetrahydrofuran | 40 | 100 | 92.5 | 3.94 | 39.9 | 1.57 |
| 6 | Diethyl ether | 40 | 100 | 89.9 | 3.78 | 40.4 | 1.82 |
| 7 | Sepasolv MPE mixtures of triethylene to decaethylene glycol methyl isopropyl ethers of the formula $CH_3O-(CH_2-CH_2-O)_{5.5}-C_3H_7$ | 40 | 100 | 92.6 | 4.0 | 39.4 | 2.15 |
| 8 | Pluriol E 200 a mixture of oxyethylated oxo-alcohols of mean molecular weight 200 | 40 | 100 | 89.6 | 3.85 | 39.6 | 2.0 |
| 9 | Pluriol P 600 a mixture of oxyethylated oxo-alcohols of mean molecular weight 600 | 40 | <100 | 93.1 | 3.0 | 53.5 | 1.82 |
| 10 | Methylal | 40 | <100 | 90.2 | 2.8 | 54.5 | 1.6 |

TABLE 2

| Example | Aerosil g | Al(NO$_3$)$_3$ .9 H$_2$O g | $SiO_2/Al_2O_3$ employed | NaOH g | Pentasil type % | $SiO_2$ found % | $Al_2O_3$ found % | $SiO_2/Al_2O_3$ found | Na$^+$ found % |
|---|---|---|---|---|---|---|---|---|---|
| 11 | 26.7 | 16.66 | 20 | 1.77 | 100 | 84.4 | 5.4 | 26.6 | 2.1 |
| 12 | 26.7 | 5.6 | 60 | 1.2 | 100 | 91.1 | 2.7 | 57.4 | 1.4 |
| 13 | 26.7 | 4.5 | 75 | 1.42 | 100 | 95.1 | 2.2 | 73.5 | 1.0 |

EXAMPLES 14-15

The zeolites prepared in Examples 1, 2 and 5 are mixed with Pural SB (boethmite) in the ratio of 60:40, using 3% of formic acid as a peptizing agent, the mixture is converted to 2 mm extrudates and this product is continuously exchanged with 20% strength NH$_4$Cl solution for 2 hours at 80° C. The ratio of zeolite to NH$_4$Cl is 1:15. The resulting NH$_4$-form of the zeolite is dried for 16 hours at 110° C. and calcined for 5 hours at 500° C. The catalysts thus obtained are employed for the gas phase alkylation of benzene with ethylene under the following conditions: $C_6H_6:C_2H_4=3:1$, WHSV=7.8 g of $C_6H_6$/g of catalyst per hour, T=400° C. The results are shown in Table 3.

EXAMPLES 16-18

The catalysts used in Examples 14 and 15, as well as the zeolite prepared in THF (mixed with Pural SB in the ratio of 60:40 and then extruded) are employed for the conversion of methanol to olefins. A methanol/$H_2O$ mixture in the ratio of 1:2 is passed under isothermal conditions over the said catalyst at 400° C., at an LHSV of 1.3 h$^{-1}$ (based on pure $CH_3OH$). The product distributions in the gas phase which are shown in Table 4 are obtained.

TABLE 3

| Example | Zeolite from Example | prepared in | Conversion of $C_6H_6$ % | Selectivity, EB based on $C_6H_6$ % | Selectivity, EB + DEB based on $C_6H_6$ % | Conversion of $C_2H_4$ % | Selectivity, EB based on $C_2H_4$ % | Selectivity, EB + DEB based on $C_2H_4$ % |
|---|---|---|---|---|---|---|---|---|
| 14 | 1 | monoglyme | 27 | 95 | 99 | 95.5 | 83 | 91 |
| 15 | 2 | diglyme | 26 | 97.5 | 99 | 96 | 80 | 89 |

EB = ethylbenzene
DEB = diethylbenzene

TABLE 4

| Example | Zeolite prepared in | Conversion of $CH_3OH$ % | $CH_4$ % by volume | $C_2H_6$ % by volume | $C_2H_4$ % by volume | $C_3H_8$ % by volume | $C_3H_6$ % by volume | $C_4^=$ % by volume | $C_4^+$ % by volume |
|---|---|---|---|---|---|---|---|---|---|
| 16 | monoglyme | 100 | 6.7 | 0.9 | 30.7 | 12.7 | 21.9 | 7.9 | 13.8 |
| 17 | diglyme | 100 | 14.5 | <0.5 | 44.8 | 4.3 | 19.7 | 3.5 | 6.4 |
| 18 | THF | 100 | 9.4 | 1.0 | 30.8 | 13.1 | 13.5 | 4.0 | 19.0 |

We claim:

1. A process for the preparation of a crystalline aluminosilicate of the pentasil type by hydrothermal crystallization of $SiO_2$ and $Al(OH)_3$, in the molar ratio of from 40 to 400 $SiO_2$ to $Al_2O_3$, in the presence of an alkali metal salt, at a concentration of from 1 to 6 moles of alkali metal salts per mole of $Al(OH)_3$, at from 80° to 250° C., wherein the crystallization is carried out in a mixture with a solvent consisting of an ether, in the concentration of from 9 to 185 moles of ether per mole of $Al(OH)_3$, selected from the group consisting of ethylene glycol dimethyl ether, diethyl ether, a mixture of triethylene to decaethylene glycol methyl isopropyl ethers, a mixture of oxyethylated oxo-alcohols, dimethoxy-methane, and a poly(ethylene glycol) dimethyl ether or a mixture of this ether with water, comprising: mixing the $SiO_2$, $Al(OH)_3$, and alkali metal salts with the solvent to form a reaction mixture; stirring the reaction mixture to render it homogeneous; and reacting said reaction mixture at from 80° to 250° C. in a closed vessel under autogenous pressure to form the crystalline aluminosilicate.

2. A process as set forth in claim 1, wherein the solvent used for the crystallization is poly(ethylene glycol) dimethyl ether.

3. A process as set forth in claim 1, wherein the solvent used for the crystallization is an ether selected from the group consisting of ethylene glycol dimethyl ether, diethylene glycol dimethyl ether, triethylene glycol dimethyl ether, tetraethylene glycol dimethyl ether, and diethyl ether, or a mixture of this ether with water.

4. A process as recited in claim 1, wherein the mixture contains 1.5 moles of alkali metal salts per mole of $Al(OH)_3$.

5. A process as set forth in claim 1, wherein a molar ratio of $SiO_2/Al_2O_3$ of from 40 to 75, and of $M_2O/Al_2O_3$ of from 1.5 to 2 is employed in the reaction mixture, M being an alkali metal.

6. A process as set forth in claim 1, wherein the solvent used for the crystallization is a particular mixture of ethers selected from the group consisting of a mixture of triethylene to decaethylene glycol methyl isopropylethers of mean degree of oxyethylation equal to 5.5 having the formula $CH_3O-(CH_2-CH_2-O)_{5.5}-C_3H$, a mixture of oxyethylated oxo-alcohols of mean molecular weight 200, a mixture of oxyethylated oxo-alcohols of mean molecular weight 600, and dimethoxymethane, or a mixture of one of these with water.

7. A process as set forth in claim 1, wherein the $SiO_2$ and the $Al(OH)_3$ are first suspended in separate portions of the solvent, and the suspension of $Al(OH)_3$ is then introduced into the suspension of $SiO_2$ to form the reaction mixture.

8. A process as set forth in claim 1, wherein the reaction mixture comprises commercial pyrogenic silica, freshly precipitated $Al(OH)_3$, and NaOH in a 50:50 by weight ether/water mixture which is reacted for 3 to 5 days, at from 150° to 170° C., under autogenous pressure in a stirred autoclave.

* * * * *